(12) United States Patent
Dunbar et al.

(10) Patent No.: US 10,188,547 B2
(45) Date of Patent: *Jan. 29, 2019

(54) APPARATUS AND METHOD FOR USING A PORTABLE THERMAL DEVICE TO REDUCE ACCOMMODATION OF NERVE RECEPTORS

(71) Applicant: CAREWAVE MEDICAL, INC., Seattle, WA (US)

(72) Inventors: Peter J. Dunbar, Mercer Island, WA (US); Charles Chabal, Bellevue, WA (US)

(73) Assignee: CAREWAVE MEDICAL, INC., Seattle, WA (US)

( * ) Notice: Subject to any disclaimer, the term of this patent is extended or adjusted under 35 U.S.C. 154(b) by 467 days.

This patent is subject to a terminal disclaimer.

(21) Appl. No.: 14/221,949

(22) Filed: Mar. 21, 2014

(65) Prior Publication Data

US 2015/0094671 A1    Apr. 2, 2015

Related U.S. Application Data

(63) Continuation of application No. 13/004,746, filed on Jan. 11, 2011, now Pat. No. 8,702,775, which is a
(Continued)

(51) Int. Cl.
*A61F 7/00* (2006.01)
*A61F 7/08* (2006.01)
(Continued)

(52) U.S. Cl.
CPC ............... *A61F 7/00* (2013.01); *A61F 7/007* (2013.01); *A61M 35/00* (2013.01);
(Continued)

(58) Field of Classification Search
CPC ..... A61F 7/00; A61F 7/007; A61F 2007/0093
See application file for complete search history.

(56) References Cited

U.S. PATENT DOCUMENTS

| 1,377,158 A | 5/1921 | Radisson |
| 3,857,397 A | 12/1974 | Brosseau |

(Continued)

FOREIGN PATENT DOCUMENTS

| WO | WO-8702891 A1 | 5/1987 |
| WO | 2005079295 A1 | 9/2005 |

(Continued)

OTHER PUBLICATIONS

International Search Report and Written Opinion International Application No. PCT/US06/04506, Applicant Carewave, Inc., dated Sep. 25, 2007, 9 pages.

*Primary Examiner* — Kaitlyn E Smith
(74) *Attorney, Agent, or Firm* — Perkins Coie LLP

(57) ABSTRACT

A system and method for portably delivering a therapeutic dose of heat to the skin to relieve pain, reduce accommodation of thermal nerve receptors, promote healing, and deliver transcutaneous medications. The heating device is user programmable or preprogrammed to deliver according to a variety of cycles, patterns and algorithms. The cycles, patterns, and algorithms of the heat are programmable parameters, are under the user's control, and increase the effectiveness and efficiency of the device. The heating algorithms are designed to interact with an individual user's thermal nerve receptors and other tissue characteristics and to reduce the tendency of the receptors to accommodate to the external stimuli with back pain, muscular pain, dysmenorrhea, headaches, fibromyalgia, post-herpetic neuralgia, nerve injuries and neuropathies, and sprains and strain. The device can also be used in conjunction with existing medical devices such as Transcutaneous Electrical Nerve Stimulators (TENS) to increase the effectiveness of TENS devices.

31 Claims, 14 Drawing Sheets

Related U.S. Application Data continuation of application No. 11/351,305, filed on Feb. 8, 2006, now Pat. No. 7,871,427.

(60) Provisional application No. 60/651,369, filed on Feb. 8, 2005.

(51) Int. Cl.
*A61M 35/00* (2006.01)
*A61N 1/36* (2006.01)
*A61F 7/02* (2006.01)

(52) U.S. Cl.
CPC .. *A61N 1/36021* (2013.01); *A61F 2007/0001* (2013.01); *A61F 2007/0002* (2013.01); *A61F 2007/0011* (2013.01); *A61F 2007/0032* (2013.01); *A61F 2007/0035* (2013.01); *A61F 2007/0042* (2013.01); *A61F 2007/0044* (2013.01); *A61F 2007/0045* (2013.01); *A61F 2007/0093* (2013.01); *A61F 2007/0285* (2013.01); *A61F 2007/0295* (2013.01)

(56) References Cited

U.S. PATENT DOCUMENTS

| | | | |
|---|---|---|---|
| 4,107,509 A | 8/1978 | Scher et al. | |
| 4,201,218 A | 5/1980 | Feldman et al. | |
| 4,245,149 A | 1/1981 | Fairlie | |
| 4,279,255 A | 7/1981 | Hoffman | |
| 4,303,074 A | 12/1981 | Bender | |
| 4,310,745 A | 1/1982 | Bender | |
| 4,348,584 A | 9/1982 | Gale et al. | |
| 4,396,011 A | 8/1983 | Mack et al. | |
| 4,398,535 A | 8/1983 | Guibert | |
| 4,518,851 A | 5/1985 | Oppitz | |
| 4,575,097 A | 3/1986 | Brannigan et al. | |
| 4,736,088 A | 4/1988 | Bart | |
| 4,930,317 A | 6/1990 | Klein | |
| 5,097,828 A | 3/1992 | Deutsch | |
| 5,138,138 A | 8/1992 | Theilacker et al. | |
| 5,336,255 A | 8/1994 | Kanare et al. | |
| 5,423,874 A | 6/1995 | D'Alerta | |
| 5,447,530 A | 9/1995 | Guibert et al. | |
| 5,451,747 A | 9/1995 | Sullivan et al. | |
| 5,580,350 A | 12/1996 | Guibert et al. | |
| 5,601,618 A | 2/1997 | James | |
| 5,658,583 A | 8/1997 | Zhang et al. | |
| 5,735,889 A | 4/1998 | Burkett et al. | |
| 5,741,318 A | 4/1998 | Ouellette et al. | |
| 5,817,145 A | 10/1998 | Augustine et al. | |
| 5,891,189 A | 4/1999 | Payne, Jr. | |
| 5,893,991 A | 4/1999 | Newell | |
| 5,906,637 A | 5/1999 | Davis et al. | |
| 5,925,072 A | 7/1999 | Cramer et al. | |
| 5,947,914 A | 9/1999 | Augustine | |
| 5,954,680 A | 9/1999 | Augustine | |
| 5,964,721 A | 10/1999 | Augustine | |
| 5,964,723 A * | 10/1999 | Augustine | A61F 7/007 602/2 |
| 5,984,995 A | 11/1999 | White | |
| 5,986,163 A * | 11/1999 | Augustine | A61F 7/007 602/2 |
| 6,010,527 A | 1/2000 | Augustine et al. | |
| 6,013,097 A | 1/2000 | Augustine et al. | |
| 6,045,518 A * | 4/2000 | Augustine | A61F 7/007 602/2 |
| 6,066,164 A | 5/2000 | Macher et al. | |
| 6,071,254 A | 6/2000 | Augustine | |
| 6,095,992 A | 8/2000 | Augustine | |
| 6,096,067 A | 8/2000 | Cramer et al. | |
| 6,110,197 A | 8/2000 | Augustine et al. | |
| 6,113,561 A * | 9/2000 | Augustine | A61F 7/007 602/2 |
| 6,146,732 A | 11/2000 | Davis et al. | |
| 6,213,965 B1 | 4/2001 | Augustine et al. | |
| 6,213,966 B1 * | 4/2001 | Augustine | A61F 7/007 602/2 |
| 6,217,535 B1 * | 4/2001 | Augustine | A61F 7/007 602/2 |
| 6,235,049 B1 | 5/2001 | Nazerian | |
| 6,241,697 B1 | 6/2001 | Augustine | |
| 6,248,084 B1 | 6/2001 | Augustine et al. | |
| 6,254,557 B1 | 7/2001 | Augustine et al. | |
| 6,264,622 B1 * | 7/2001 | Augustine | A61F 7/007 602/2 |
| 6,267,740 B1 | 7/2001 | Augustine et al. | |
| 6,283,931 B1 | 9/2001 | Augustine | |
| 6,293,917 B1 | 9/2001 | Augustine et al. | |
| 6,331,695 B1 | 12/2001 | West | |
| 6,353,211 B1 | 3/2002 | Chen | |
| 6,406,448 B1 * | 6/2002 | Augustine | A61F 7/007 602/2 |
| 6,407,307 B1 * | 6/2002 | Augustine | A61F 7/007 602/2 |
| 6,419,651 B1 * | 7/2002 | Augustine | A61F 7/007 602/2 |
| 6,423,018 B1 * | 7/2002 | Augustine | A61F 7/007 602/2 |
| 6,436,063 B1 | 8/2002 | Augustine et al. | |
| 6,465,709 B1 | 10/2002 | Sun et al. | |
| 6,468,295 B2 | 10/2002 | Augustine et al. | |
| 6,485,506 B2 | 11/2002 | Augustine | |
| 6,567,696 B2 | 5/2003 | Voznesensky | |
| 6,572,871 B1 | 6/2003 | Church et al. | |
| 6,580,012 B1 | 6/2003 | Augustine et al. | |
| 6,605,012 B2 | 8/2003 | Muller | |
| 6,710,313 B1 | 3/2004 | Asami et al. | |
| 6,716,235 B2 | 4/2004 | Augustine et al. | |
| 6,840,915 B2 * | 1/2005 | Augustine | A61F 7/007 602/2 |
| 6,893,453 B2 | 5/2005 | Agarwal et al. | |
| 6,921,374 B2 * | 7/2005 | Augustine | A61F 7/007 602/2 |
| 6,925,317 B1 | 8/2005 | Samuels | |
| 7,022,093 B2 | 4/2006 | Smith et al. | |
| 7,783,361 B2 | 8/2010 | Docherty et al. | |
| 7,871,427 B2 * | 1/2011 | Dunbar | A61F 7/007 607/108 |
| 8,579,953 B1 | 11/2013 | Dunbar et al. | |
| 8,702,775 B2 * | 4/2014 | Dunbar | A61F 7/007 607/108 |
| 2001/0037104 A1 * | 11/2001 | Zhang | A61K 9/0004 604/502 |
| 2002/0026226 A1 | 2/2002 | Ein | |
| 2002/0183813 A1 | 12/2002 | Augustine et al. | |
| 2003/0013998 A1 * | 1/2003 | Augustine | A61F 7/007 602/2 |
| 2003/0069618 A1 | 4/2003 | Smith et al. | |
| 2004/0073258 A1 | 4/2004 | Church et al. | |
| 2004/0211569 A1 | 10/2004 | Vinegar et al. | |
| 2006/0195168 A1 | 8/2006 | Dunbar et al. | |
| 2006/0258962 A1 | 11/2006 | Kopanic et al. | |
| 2010/0036445 A1 | 2/2010 | Sakai et al. | |
| 2011/0279963 A1 | 11/2011 | Kumar et al. | |

FOREIGN PATENT DOCUMENTS

| | | |
|---|---|---|
| WO | 2006086513 A2 | 8/2006 |
| WO | 2008057884 A2 | 5/2008 |

* cited by examiner

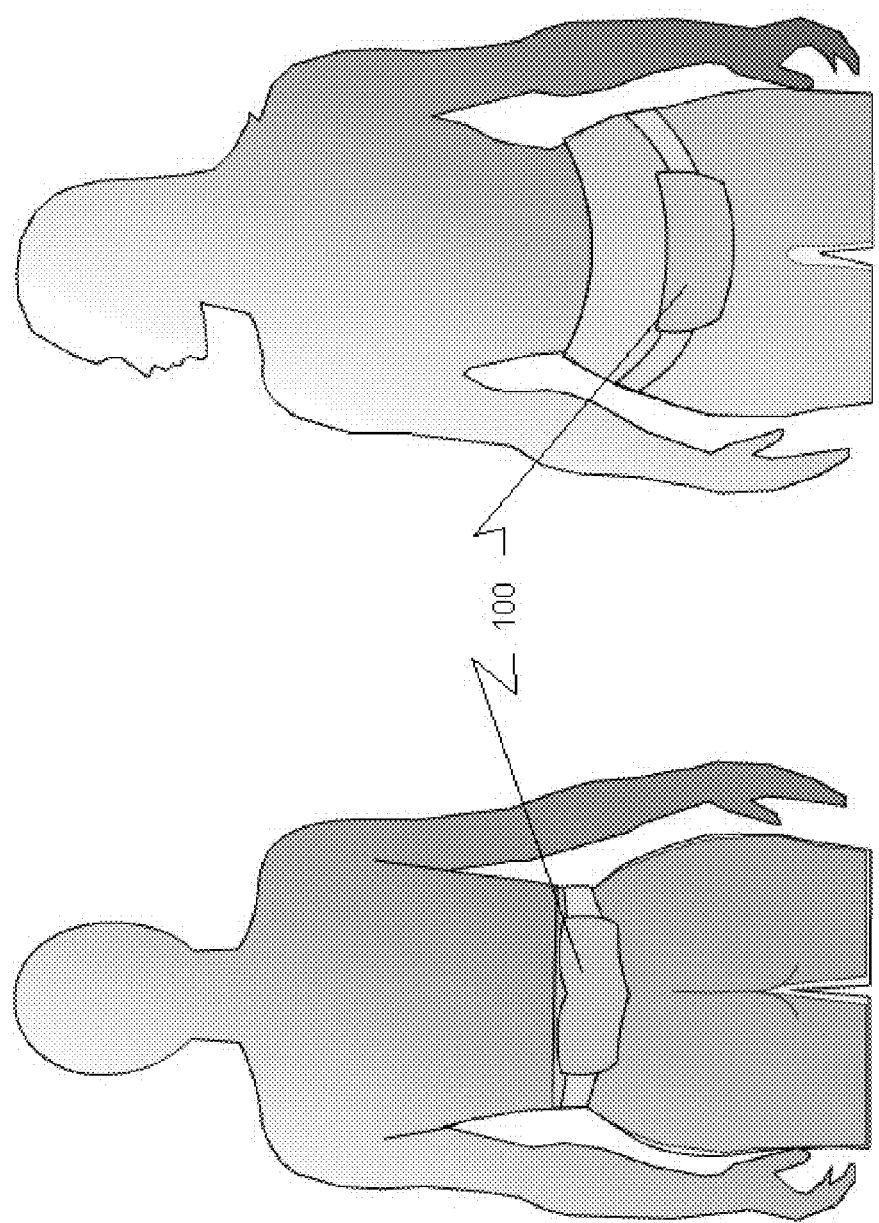

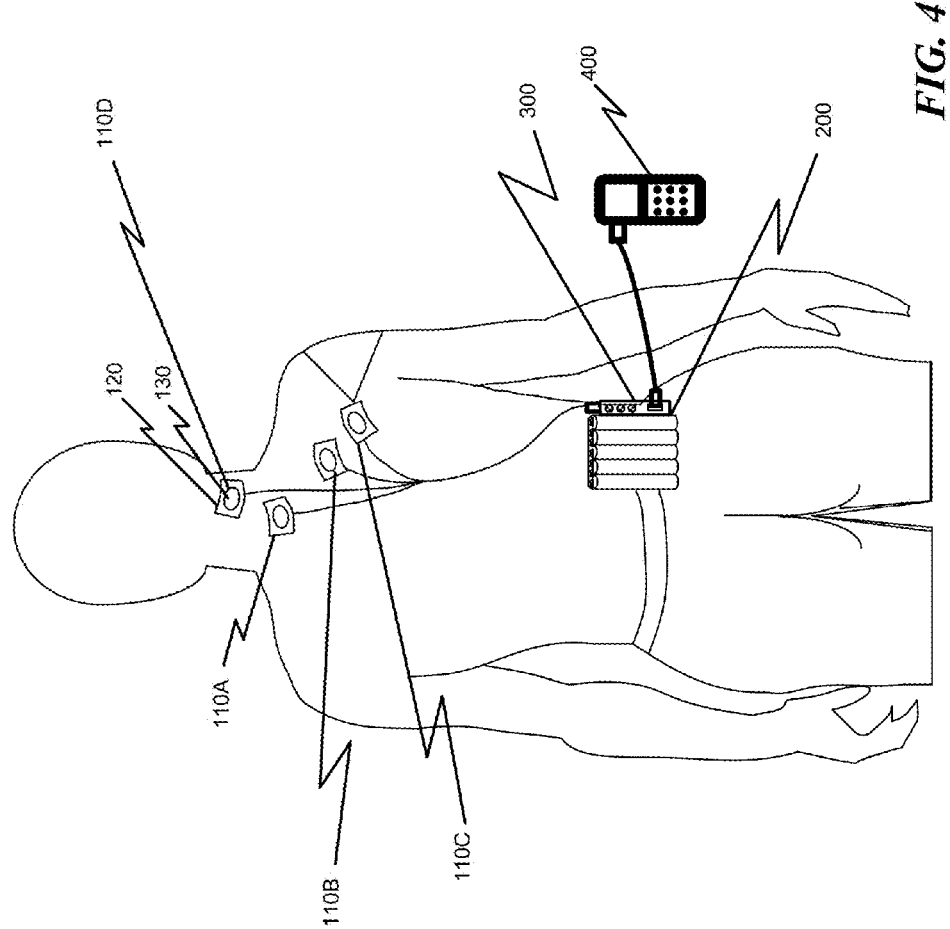

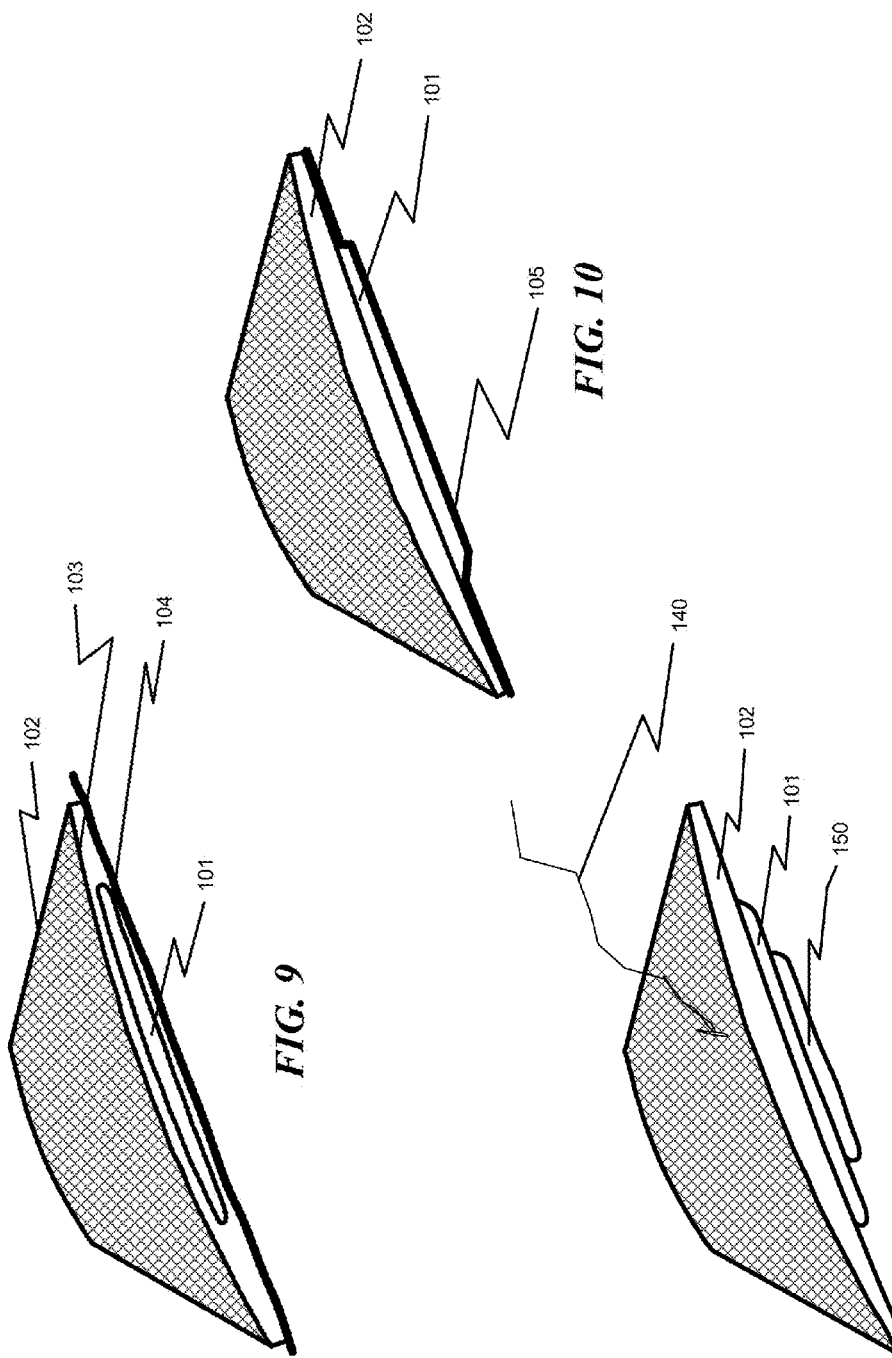

APPARATUS AND METHOD FOR USING A PORTABLE THERMAL DEVICE TO REDUCE ACCOMMODATION OF NERVE RECEPTORS

CROSS-REFERENCE TO RELATED APPLICATION(S) INCORPORATED BY REFERENCE

This application is a continuation of U.S. patent application Ser. No. 13/004,746, filed on Jan. 11, 2011 (now U.S. Pat. No. 8,702,775), entitled "APPARATUS AND METHOD FOR USING A PORTABLE THERMAL DEVICE TO REDUCE ACCOMMODATION OF NERVE RECEPTORS," which is a continuation of U.S. patent application Ser. No. 11/351,305, filed Feb. 8, 2006 (now U.S. Pat. No. 7,871,427), entitled "APPARATUS AND METHOD FOR USING A PORTABLE THERMAL DEVICE TO REDUCE ACCOMMODATION OF NERVE RECEPTORS," which claims the benefit of U.S. Provisional Patent Application No. 60/651,369, filed on Feb. 8, 2005, entitled "PROGRAMMABLE PORTABLE CONTACT ANALGESIC AND DRUG DELIVERY HEATING DEVICE WITH MODE OF ACTION AND HEATING ALGORITHMS". Each of these applications are incorporated herein in by reference in their entirety.

TECHNICAL FIELD

The present invention relates to using a portable thermal device to reduce accommodation of thermal nerve receptors, for example, a user-controllable variable-heat cycle thermal device.

BACKGROUND

In 1965, Melzack and Wall described the physiologic mechanisms by which stimulation of large diameter non-pain sensory nerves could reduce the amount of unpleasant activity carried by pain nerves. This landmark observation published in Science was termed the "gate control theory" and offered a model to describe the interactions between various types of the sensory pathways in the peripheral and central nervous systems. The model described how non-painful sensory input such as mild electrical stimulation could reduce or gate the amount of nociceptive (painful) input that reached the central nervous system.

The gate-control theory stimulated research that lead to the creation of new medical devices such as transcutaneous electrical nerve stimulators (TENS). In brief, TENS works by electrically "blocking" pain impulses carried by peripheral nerves. Receptors to cold and heat are located just below the surface of the skin. Heat receptors are activated through a temperature range of about 36° C. to 45° C. and cold receptors by a temperature range about 1-20° C. below the normal skin temperature of 34° C. (Van Hees and Gybels, 1981). The stimuli are transmitted centrally by thin poly-modal C nerve fibers. Activation of heat receptors are also affected by the rate of rise of the heat stimuli (Yamitsky et al., 1992). Above 45° C. warm receptor discharge decreases and nociceptive response increases producing the sensations of pain and burning (Torebjork et al., 1984).

Activation of poly-modal thermal receptors causes significant pain relief in controlled experimental conditions. Kakigi and Watanabe (1996) demonstrated that warming and cooling of the skin in Human volunteers could significantly reduce the amount of reported pain and somatosensory evoked potential activity induced by the noxious stimulation of a $CO_2$ laser. The authors offered that the effects seen could be from a central inhibitory effect produced by the thermal stimulation. Similar inhibition of pain from thermal simulation was reported in a different Human experimental pain model (Ward et al., 1996). The study authors (Kakigi and Watanabe 1996 and Ward et al., 1996) proposed that the thermal analgesia was in part from a central inhibitory effect (gating) from stimulation of small thin C nerve fibers. This contrasts with TENS which produces at least part of its analgesia through gating brought on by activation of large diameter afferent nerve fibers.

A number of recent clinical studies strongly support the use of heat as an analgesic in patients who suffer from chronic pain and offer potential mechanisms by which heat produces analgesia. Abeln et al. (2000) in a randomized controlled single-blinded study examined the effect of low level topical heat in 76 subjects who suffered from low back pain. Heat treatment was statistically more effective in relieving pain and improving the quality of sleep than that produced by placebo.

Weingand et al. (2001) examined the effects in a randomized, single blinded, controlled trial of low level topical heat in a group of over 200 subjects who suffered from low back pain and compared heat to placebo heat, an oral analgesic placebo, and ibuprofen 1200 mg/day. The authors found heat treatment more effective than placebo and superior to ibuprofen treatment in relieving pain and increasing physical function as assessed by physical examination and the Roland Morris disability scale.

A separate group (Nadler at al, 2002) found similar results in a prospective single blinded randomized controlled trial of 371 subjects who suffered from acute low back pain. The authors found that cutaneous heat treatment was more effective than oral ibuprofen 1200 mg/day, acetaminophen 4000 mg/day or oral and heat placebos in producing pain relief and improving physical function. The authors offered several hypotheses for the mechanism(s) of action which includes increased muscle relaxation, connective tissue elasticity, blood flow, and tissue healing potential provided through the low-level topical heat. Similar beneficial effects of topical heat were show in patients who suffered from dysmenorrhea (Akin et al., 2001), and temporomandibular joint pain TMJ (Nelson et al., 1988).

A recent study used power Doppler ultrasound to evaluate the effects of topical heat on muscle blood flow in Humans (Erasala et al., 2001). Subjects underwent 30 minutes of heating over their trapezius muscle and changes in blood flow were examined at 18 different locations over the muscle. Vascularity increased 27% (p=0.25), 77% (p=0.03) and 104% (p=0.01) with 39, 40 or 42° C. temperature of the heating pad. Importantly increases in blood flow extended approximately 3 cm deep into the muscle. The authors concluded that the increased blood flow likely contributed to the analgesic and muscle relaxation properties of the topical heat. Similar increases in deep vascular blood flow were noted using magnetic resonance thermometry in subjects treated with mild topical heat by two separate groups (Mulkern et al., 1999, and Reid et al., 1999).

TENS, Heat, and Pain Relief Methods

Recent studies demonstrating the analgesic effectiveness of heat and provided potential mechanisms of action. The mechanisms include a reduction of pain through a central nervous system interaction mediated via thin c-fibers (Kakigi and Watanabe, 1996, Ward et al., 1996), enhancement of superficial and deeper level blood flow (Erasala et al., 2001, Mulkern et al., 1999, Reid et al., 1999), or local effects on the muscle and connective tissue (Nadler et al., 2002, Akin et al. 2001). TENS is thought to act through inhibition of nociception by increasing endogenous opioids or by a neural inhibitory interaction of nociception via large diameter fibers. TENS is widely used and endorsed by the pain management guidelines of both the AHCPR and American Geriatric Society (Gloth 2001). However a significant number of patients fail to achieve adequate relief with TENS or fail within six months of starting treatment (Fishbain et al., 1996).

Previous Work

Many devices beginning with the earliest of the resistive wire heating pads are well known to accomplish the individual function of heating. A more complex therapeutic device for providing heating or cooling of the skin and underlying body tissue is disclosed in Deutsch (U.S. Pat. No. 5,097,828). This device includes a handle and a thermally conductive head that utilizes Peltier effect devices for heating or cooling a contact plate. The contact plate may also be connected to a high-voltage source for electrical stimulation.

Kanare et al. (U.S. Pat. No. 5,336,255), describes an electrical stimulation and heating or cooling pack that includes a pouch and straps for positioning and holding the pouch against a body part. Flexible conductive patches attached to the pouch are connectable to a remote pulse generator. An electrically conductive adhesive gel pad is also provided for coupling the conductive patch to the body part.

Heath (U.S. Pat. No. 1,377,158), describes an electrical resistance unit which can adapt to many uses, including heating devices. James (U.S. Pat. No. 5,601,618) is a device for providing combination electrical stimulation and the simultaneous heating of the body tissue. The device is a single unit and is portable, relying upon low current dry battery power for heating.

BRIEF DESCRIPTION OF THE DRAWINGS

In this description, a Patient Controlled Thermal Analgesia (PTCA) device is presented and further discussed below. For convenience, the device may be referred to as a PTCA, a heating device, a portable thermal device or a user-controllable heating device or some combination of these terms; however, use of these terms is not intended, and should not be taken, to exclude from the scope of this invention other types of heat sources that are designed to be placed on the skin to enable increased thermal stimulation, reduce accommodation of thermal receptors, and to provide pain relief.

FIGS. 3A and 3B are rear and front views respectively of a subject wearing the heating device in accordance with embodiments of the invention.

FIG. 4 is a rear view of a subject wearing a plurality of spaced apart thermal heating elements; the thermal heating elements are individually controlled by a single controller in accordance with embodiments of the invention.

FIG. 9 is an isometric view of a heating element having a layered design wherein cloth is in contact with the skin of a subject in accordance with embodiments of the invention.

FIG. 10 is an isometric view of a heating element having an alternative layered design wherein conductive gel is in contact with the skin of a subject in accordance with embodiments of the invention.

FIG. 11 is an isometric view of heating element having a yet another alternative layered design which further includes a drug delivery or a TENS connection system in contact with skin in accordance with embodiments of the invention.

Figure 1B:
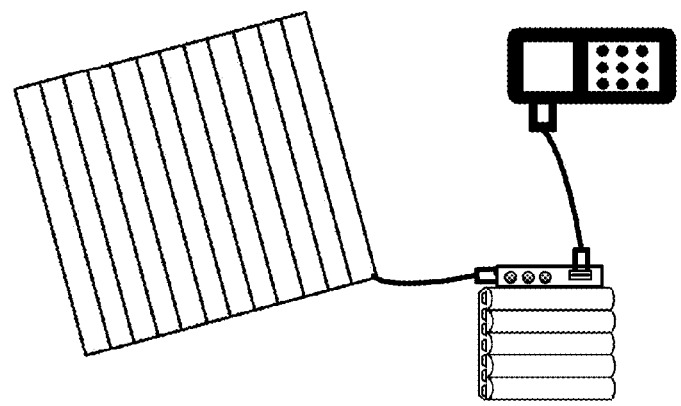
FIGS. 1A and 1B are isometric views of a heating device including thermal elements having thermal zones, a controller and a power source in accordance with embodiments of the invention.

In the drawings, identical reference numbers identify similar elements or acts. The sizes and relative positions of elements in the drawings are not necessarily drawn to scale, and some of these elements are arbitrarily enlarged to improve drawing legibility. Further, the particular shapes of the elements as drawn are not intended to convey any information regarding the actual shape of the particular elements, and have been solely selected for ease of recognition in the drawings.

DETAILED DESCRIPTION

A. Overview

The invention will now be described with respect to various embodiments. The present disclosure describes devices, systems, and methods for using heat to relieve pain and to render existing devices, for example, TENS, more effective. The following description provides specific details for a thorough understanding of, and enabling description for, these embodiments of the invention. However, one skilled in the art will understand that the invention may be practiced without these details. In other instances, well-known structures and functions have not been shown or described in detail to avoid unnecessarily obscuring the description of the embodiments of the invention.

The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this Detailed Description section. Additionally, the invention can include other embodiments that are within the scope of the claims, but are not described in detail with respect to FIGS. 1-18.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, or characteristics may be combined in any suitable manner in one or more embodiments.

The terms used herein are not intended, and should not be taken, to exclude from the scope of this invention other types of heat sources that are designed to be placed on the skin to enable pain relief. Illustrative embodiments will be shown and described; however, one skilled in the art will recognize that the illustrative embodiments do not exclude other embodiments.

The headings provided herein are for convenience only and do not interpret the scope or meaning of the claimed invention.

One aspect is directed toward a portable heating device that uses heat to relieve pain and allows users to program and customize settings and output of the heating device. The heating device portably delivers a therapeutic dose of heat to the skin to reduce accommodation of thermal nerve receptors and includes a portable heat delivery element, a power source and a microprocessor control unit. Additionally, the portable heat delivery element may be contained within a housing and the housing may be adaptable to be worn proximate to the skin of a user. The power source is electrically coupled to the portable heat delivery element to provide a power supply to the heat delivery element. The microprocessor control unit is operably connected to the portable heat delivery element.

Another aspect is directed toward a heat delivery element that uses a variety of heating cycles and algorithms to increase the efficiency and effectiveness of the device. Accordingly, the control unit has an activation element moveable between a first on-position and a second off-position to allow a user to control activation of the control unit. Thus, the heat delivery element may be designed so a user has the option of requesting a heating cycle by simply pressing an activation device such as a button, pressure sensor or lever on the controller. The benefits of user control are supported by experience gained over the last 15 years with patient controlled analgesia devices (PCA). PCAs are computer controlled pumps that deliver intravenous pain medications and studies indicate that a patient's ability to request analgesia only when he or she needs it is a highly rated feature (Etches, 1999 and Rawal, 1999). The patient is able to tailor the amount of drug delivered over time according to his or her own needs. The device described herein can apply heat as requested by the user. According to another aspect, the control unit also includes at least one of a predetermined variable heat cycle, the variable heat cycle having at least a ramp-up phase, a steady heat phase, a ramp-down phase and a soak heat phase, wherein the temperature differential between the steady heat phase and the soak heat phase is less than 5° C., and wherein the soak heat phase is greater than basal body temperature.

Another aspect is directed toward an improvement to existing pain relief mechanisms such as TENS, analgesics related to the Gate Theory of pain stimulation of subcutaneous receptors and changes in tissue blood flow, and transcutaneous drug delivery. The heating device therefore may further include a TENS system for providing a patient relief from pain through electrical stimulation. Alternatively, the heating device may further include an analgesic cream, a nonsteroidal anti-inflammatory drug (NSAID), antidepressant medications such as topical doxepin, or an Opioid analgesic applied to the skin prior to application of the heating device.

Another aspect is directed toward a user-controllable therapeutic heating device having multiple thermal elements for relieving pain in more than one locator on the user. The therapeutic heating device has a plurality of spaced apart thermal elements for transferring heat to skin, a power source, and a control unit. The thermal elements have a first side and a second side, the first side having a heat exchanging surface in thermal communication with the skin. The control unit is operatively coupled to the thermal elements to allow the user to control the heating device. The control unit has an activation device and the activation device allows the user to initiate a heating cycle and/or pattern to activate the thermal elements according to a predetermined heating cycle and/or pattern. According to aspects of the embodiment, the thermal elements are configured to be placed in various locations on the skin to provide therapeutic heat treatment for relieving pain.

Another aspect is directed toward a method of using heat to reduce accommodation of thermal nerve receptors of a subject. The method includes increasing the temperature of a heating element to provide a first temperature ramp-up period, holding the temperature of the heating element at a predetermined first predetermined therapeutic level for at least thirty seconds, decreasing the temperature of a heating device during a ramp-down period, and holding the temperature of the heating device at a second predetermined soak level, wherein the soak level temperature is above a basal temperature, wherein the soak level temperature is less than the therapeutic level temperature by at least 1° C.

B. System for Using Heat to Reduce Accommodation of Thermal Receptors

An apparatus and method for controlled delivery of heating to the skin may include a microprocessor controller unit, a power source and housing, and a heating element or pad. The microprocessor control unit may be a programmable component that controls the device and allows the user adjustability of a variety of parameters such as the duration of heating cycle and pattern, temperature of the heating element, soak temperature and duration, shape and duration of heating wave and/or the rate of the temperature rise and fall. The predetermined or preset heating algorithms that may be contained in the microprocessor control unit are designed to increase the effectiveness and efficiency of the device. According to additional aspects, the microprocessor control unit may further include a safety mechanism to control maximum temperature, for example, the device may use a mechanical temperature fuse as a safety backup. Additionally, the heat delivery device may be configured to be a wearable portable device. Furthermore, the heat delivery device may be designed to use rechargeable or disposable batteries or may be used multiple times.

Figure 1A:
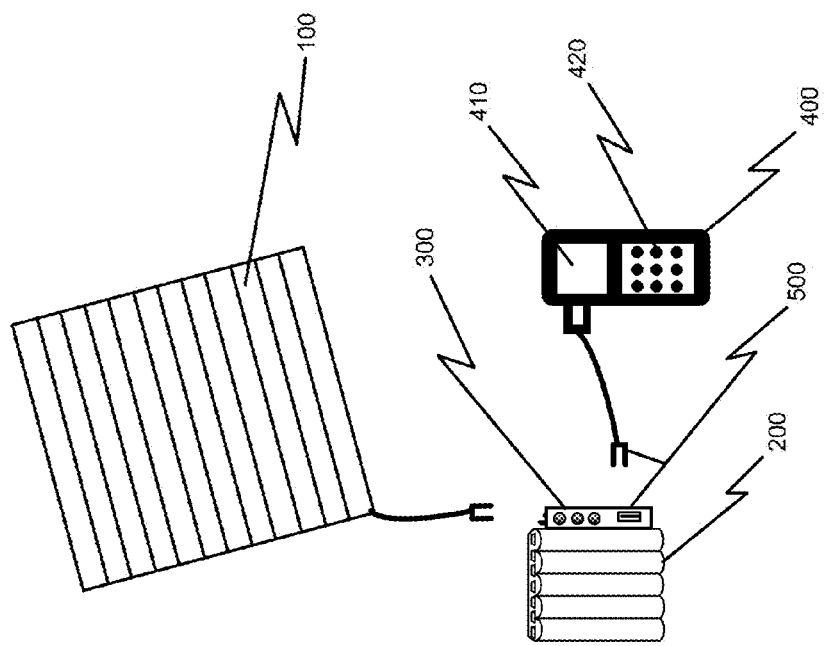

Heat is delivered through heating elements that are designed in a variety of shapes and patterns. In one example, the heating elements are thermal elements, discrete heating elements contained in zones, sections, or regions. The thermal elements are designed for placement on a variety of anatomically separate locations of the body. In one example, the heating elements may be held to the body via specially designed belts, reflective material, and clothing or attached via adhesive-like jells. A variety of jells and compounds may be placed on the heating elements or pads that aid with heat conductivity, adhesion, or contain active medications. The heating elements are designed to function as a reservoir for these jells and medications. The heat delivered by the device assists in the transcutaneous delivery of these medications. The device is designed to relieve pain or assist with healing in a variety of medical conditions such as low, mid, or upper back pain, muscular pain, dysmenorrhea, headaches, fibromyalgia, post-herpetic neuralgia, nerve injuries and neuropathies, injuries to extremities, and sprains and strains FIGS. 1A and 1B are isometric views of a heating element 100 including thermal elements having thermal zones, a controller and a power source. As shown in FIGS. 1A and 1B, the heating element or pad 100 is electrically connected to the power source 200. A programmable controller 300 is user controllable and is operably connected to the power source 200 either by a direct wired connect, a wireless connection or as is otherwise known in the art. A programming unit 400 may be used to control the programmable controller 300. The programming unit 400 may be connected to the programmable controller by direct wired connection, a plug and socket arrangement 500, a wireless connection (not shown), or as is otherwise know in the art. In this embodiment the heating element power source and programmable controller are all portable.

Figure 5:
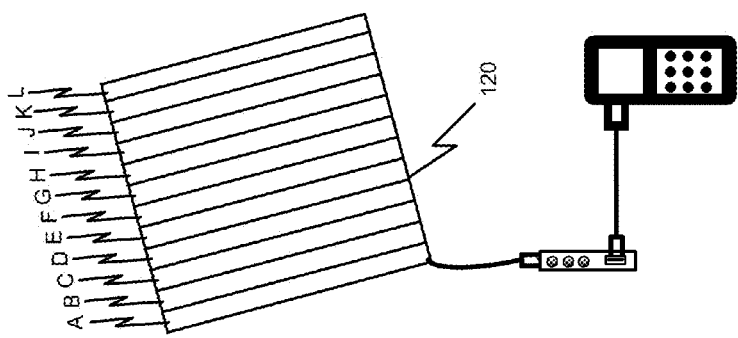
FIG. 5 is a top view of a heating device having heating elements in a vertically aligned thermal zone layout wherein each zone is individually controlled in accordance with embodiments of the invention.

The heating element may further includes zones A, B, C, D, E, F, G of independently activated thermal zones, described further with respect to FIG. 5. The thermal zones may be activated in a predetermined pattern, or may be activated at one time, or may be selectively activated as directed by the user. The pattern may be a checkerboard pattern, a sequential bar pattern, a wave pattern and/or a random pattern across the heat delivery element.

A plug and socket arrangement may be plugged into the power source, such as a battery, while the unit is operational, the plug and socket may further be connected to the programming unit 400 while it is being programmed. A switch may be built into the programmable controller 300, the plug and socket arrangement 500 may be built into the programmable controller 300 or vice versa.

The programming unit 400 can monitor process parameters via sensors (not shown) placed proximate to the heating device 100 and adjust the temperature based on the process parameters. Process parameters include but are not limited to the temperature of the heating device, the duration of the cycle, the ramp-up or ramp-down phase duration, the hold or soak phase duration, the duration of the pattern (in which multiple cycles can continuously or intermittently run), the duration, sequence and pattern of the thermal zones, and the like. The programming unit 400 can include any processor, microprocessor, hand-held microcomputer, integrated circuit, Programmable Logic Controller, Distributed Control System, and the like.

In another aspect, the programmable controller 300 or the programming unit 400 can be activated by an activation device. The activation device can include a keyboard, a mouse, a touch screen, a push button, a switch, a potentiometer, and any other devices suitable for accepting user input. The programmable controller may further include an output device 410, the output device 410 can include a display screen, a printer, a medium reader, an audio device, and any other devices suitable for providing user feedback. The programmable controller may further include a control panel 420. The control panel 420 can include indicator lights, numerical displays, and audio devices. In the embodiment shown in FIG. 1, the programming unit 400, the programmable controller 300, the power source 200 and the heating element 100 are portable. In another embodiment, the various components can be fixedly mounted to a brace, bandage or other therapeutic device.

Figure 2:
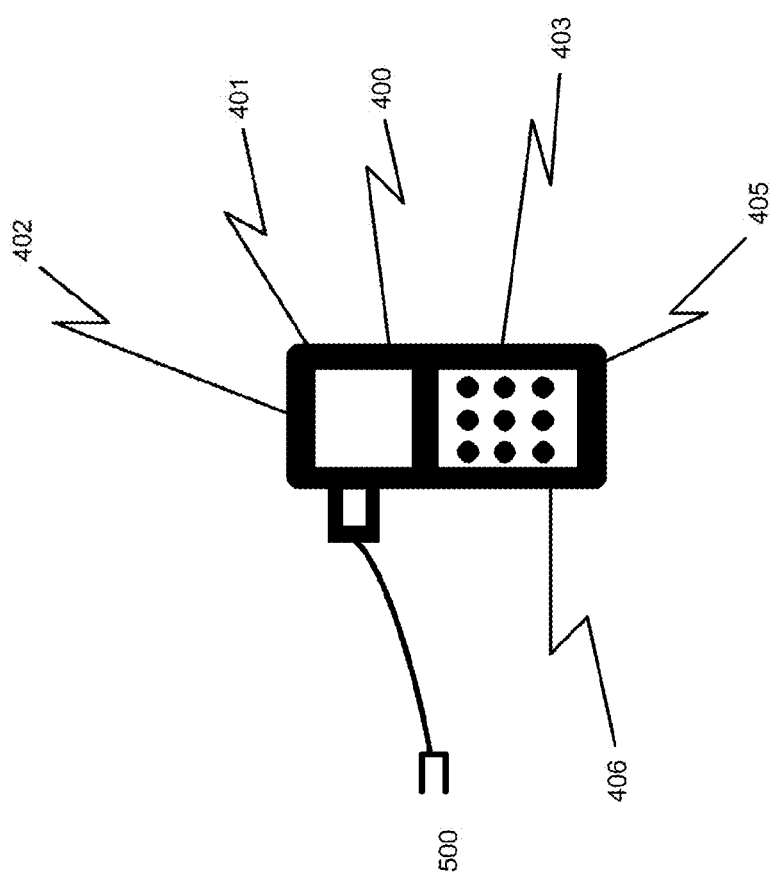
FIG. 2 is a top view of a programming unit in accordance with an embodiments of the invention.

FIG. 2 shows an example of a programming unit 400 in accordance with an embodiment of the invention. The programming unit 400 shown in FIG. 2 includes a display panel 401, an optional touch screen 402, a casing 403, controlling buttons or switches 405, power input socket 406, heating connection 404 that connects the programming unit 400 to the plug and socket arrangement 500. In this embodiment the user would program the controller 300 using the programming unit 400.

FIGS. 3A and 3B are rear and front views respectively of a subject wearing the heating device in accordance with embodiments of the invention. FIGS. 3A and 3B illustrate two body locations that a heat pad may be applied to, however, one skilled in the art will understand that there are an infinite number of possible beneficial sites on a user. Placement location of the heating device may vary between patients and between pain locations and etiologies. Placement locations may include locations along acupuncture meridians, trigger points, joints, tendons, and other such potential body locations.

In an alternative embodiment, FIG. 4 shows a rear view of a subject wearing a plurality of spaced apart thermal heating elements, the thermal heating elements may be individually controlled by a single controller or each thermal heating element may be controlled by an independent controller. As contrasted with FIG. 3 which illustrates a larger pad 100, FIG. 4 illustrates smaller heating pad or thermal elements 110a, 110b, 110c, 110d. The smaller thermal elements 110a, 110b, 110c, 110d are applied over the trapezius as may be used for headache or neck pain. Each individual thermal element 110a, 110b, 110c, 110d could be controlled by the processor 300 to deliver rotating patterns of heating. In general, and as applied to all embodiments, any number of thermal elements may be placed in an infinite number of possible beneficial sites on a user's body.

Figure 7:
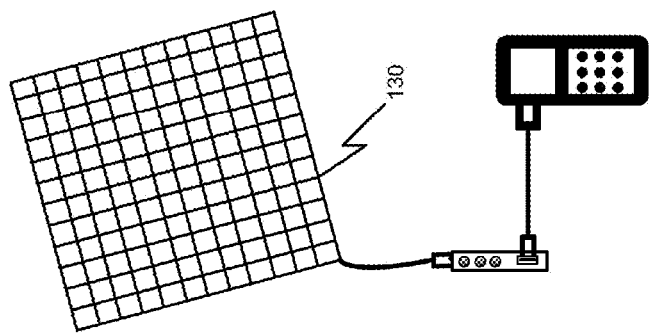
FIG. 7 is a top view of a heating device having heating elements with a thermal region layout wherein each thermal is individually controlled in accordance with embodiments of the invention.
Figure 6:
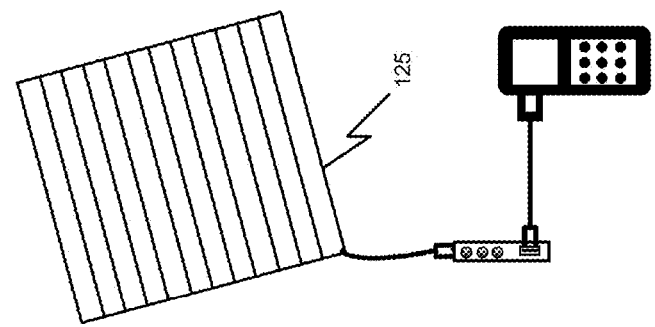
FIG. 6 is a top view a heating device having heating elements with a horizontally aligned thermal zone layout wherein each zone is individually controlled in accordance with embodiments of the invention.

In an alternative embodiment the heat could be applied to the pad in a non-uniform manner. FIG. 5 shows a top view of a heating device having heating elements in vertically aligned thermal zones A, B, C, D, E, F, G, H, I, J, K, L wherein each zone may be individually controlled. FIG. 6 shows a top view a heating device having heating elements with horizontally aligned thermal zones A, B, C, D, E, F, G, H, I, J, K, L wherein each zone may be individually controlled. FIG. 7 shows a top view of a heating device having heating elements with a thermal layout wherein each thermal may be individually controlled. FIGS. 5, 6 and 7 illustrate horizontal heating zones or bands 120, vertical heating bands 125 and thermal region layouts 130 respectively. Each zone, band or region may be individually controllable by the controller, may be preprogrammed, may be controlled in blocks, or may be controlled in a combination of user-control and preprogrammed control. Each zone, band or region may be associated with an activation device, alternatively, one activation device may operate to turn each zone, band or region on/off.

Figure 8:
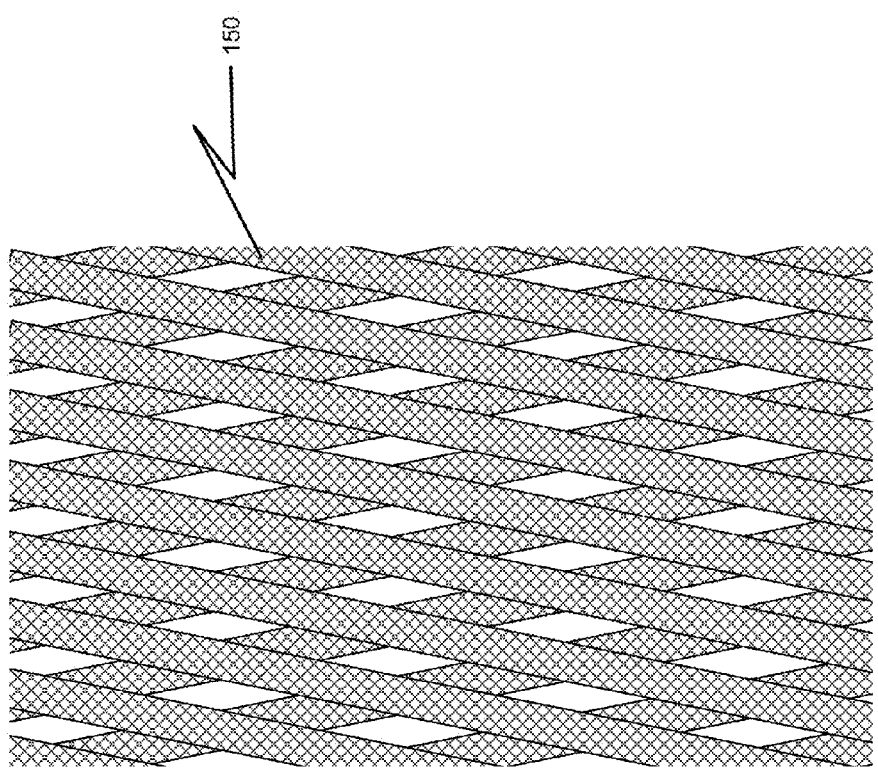
FIG. 8 is a top view of a mesh or flexible heating element having a woven configuration that can be heated in zones or regions as illustrated in FIGS. 5-7 in accordance with embodiments of the invention.

FIG. 8 shows an alternative embodiment of a mesh or flexible heating element having a woven configuration that can be heated in zones, bands, or regions as discussed with respect to FIGS. 5-8.

FIG. 9 shows a heating element having a layered design wherein cloth is in contact with the skin of a subject. The heating element and backing may be contained in a cloth pouch inside a garment 102 or belt that holds an element in a desired location. According to aspects of this embodiment, a reflective backing 103 can be incorporated to minimize heat loss, to save energy and to reduce heat capacity. Additionally, the cloth layer 104 may be disposable or reusable or part of another layer of clothing or made of materials with special properties such as but not limited to electrical or thermal conductivity.

FIG. 10 shows a heating element having an alternative layered design wherein conductive gel or jelly 105 between the heating element and the skin of a subject. According to aspects of this embodiment, the jelly could conduct heat, electricity, or both, and it could be strongly or lightly adherent. Additionally, the jelly could be a thick or thin layer and could contain therapeutic substances in solution suspension or gel.

FIG. 11 shows an alternative embodiment of a heating element that incorporates a TENS connection 140 to a conductive pad 150. According to aspects of this embodiment, an analgesic compound may be placed between the heating element and the skin. The use of TENS is designed to increase analgesic efficacy and the drawing implies electrical conductivity through a variety of means. Thus, according to aspects of this embodiment, this system could use the controllability of heat to regulate the delivery and or absorption of therapeutic substances into the skin and circulation. Examples of substances that could be regulated and delivered in this way include local anesthetics, analgesics, medications used to treat pain from nerve injuries and counter irritants. Lidocaine, fentanyl doxepin, and capsaicin are examples of such substances.

Figure 12:
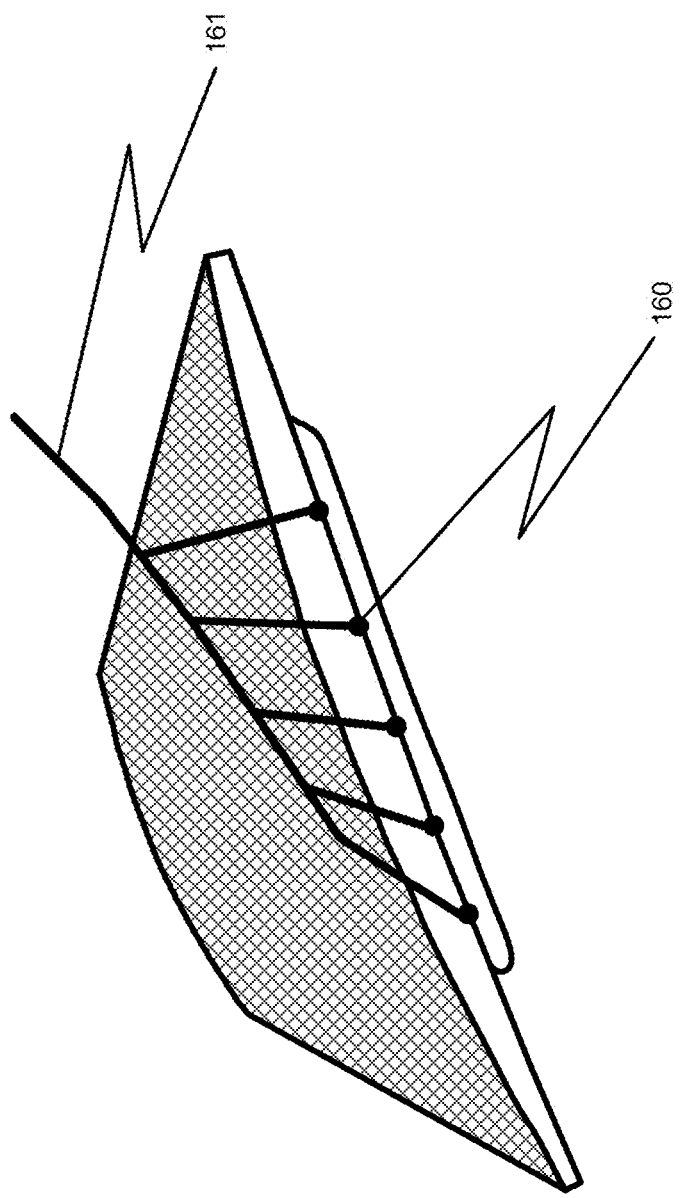
FIG. 12 is an isometric view of an alternative design of a heating element having a thermal sensing element such as a thermistor for controlling the temperature in accordance with embodiments of the invention.

The embodiments described herein may employ a variety of safety mechanisms to prevent overheating. FIG. 12 shows a sensing element 160 such as heat regulating thermistors incorporated into the heating unit with an electrical connection to the controller 161. A fuse based safety system is not shown in the picture but would add an additional layer of safety. Alternative sensing elements 160 proximate to the heat exchanging surface may be used. The sensing element 160 may be generally flush with the heat exchanging surface. Alternatively, it may be recessed or protrude from the surface. The sensing element 160 can include a temperature sensor, a transmissivity sensor, a bio-resistance sensor, an ultrasound sensor, and optical sensor, an infrared sensor, or any other desired sensor. In one example, the sensing element 160 can be a temperature sensor configured to measure the temperature of the first heat exchanging surface of the heating element and/or the temperature of the skin of the subject (not shown). Examples of suitable temperature sensors include thermocouples, resistance temperature devices, thermistors (e.g., neutron-transmutation-doped germanium thermistors), and infrared radiation temperature sensors. In another example, the sensing element 160 can be an ultrasound sensor. In yet another example, the sensing element can be an optical or infrared sensor. The sensing element 160 can be in electrical communication with the processing unit, for example, a direct wired connection and/or a wireless connection.

C. Methods of Using Heat to Reduce Thermal Accommodation Receptors

Another aspect is directed toward a method of using heat to reduce accommodation of thermal receptors on the skin of a subject. The method includes increasing the temperature of a heating element to provide a first temperature ramp-up period, holding the temperature of the heating element at a predetermined first predetermined therapeutic level for at least thirty seconds, decreasing the temperature of a heating device during a ramp-down period, and holding the temperature of the heating device at a second predetermined soak level, wherein the soak level temperature is above a basal temperature, wherein the soak level temperature is less than the therapeutic temperature level by at least 1° C.

In operation, the heating device may deliver heat intermittently. The heat may be applied for a period long enough to heat the skin to a desired level; upon reaching the desired skin temperature the device turns off and the skin is allowed to cool; after a preprogrammed interval the device may reactivate the heat unit and the cycle repeats. Alternatively, multiple cycles may be delivered sequentially for a predetermined duration.

Figure 13:
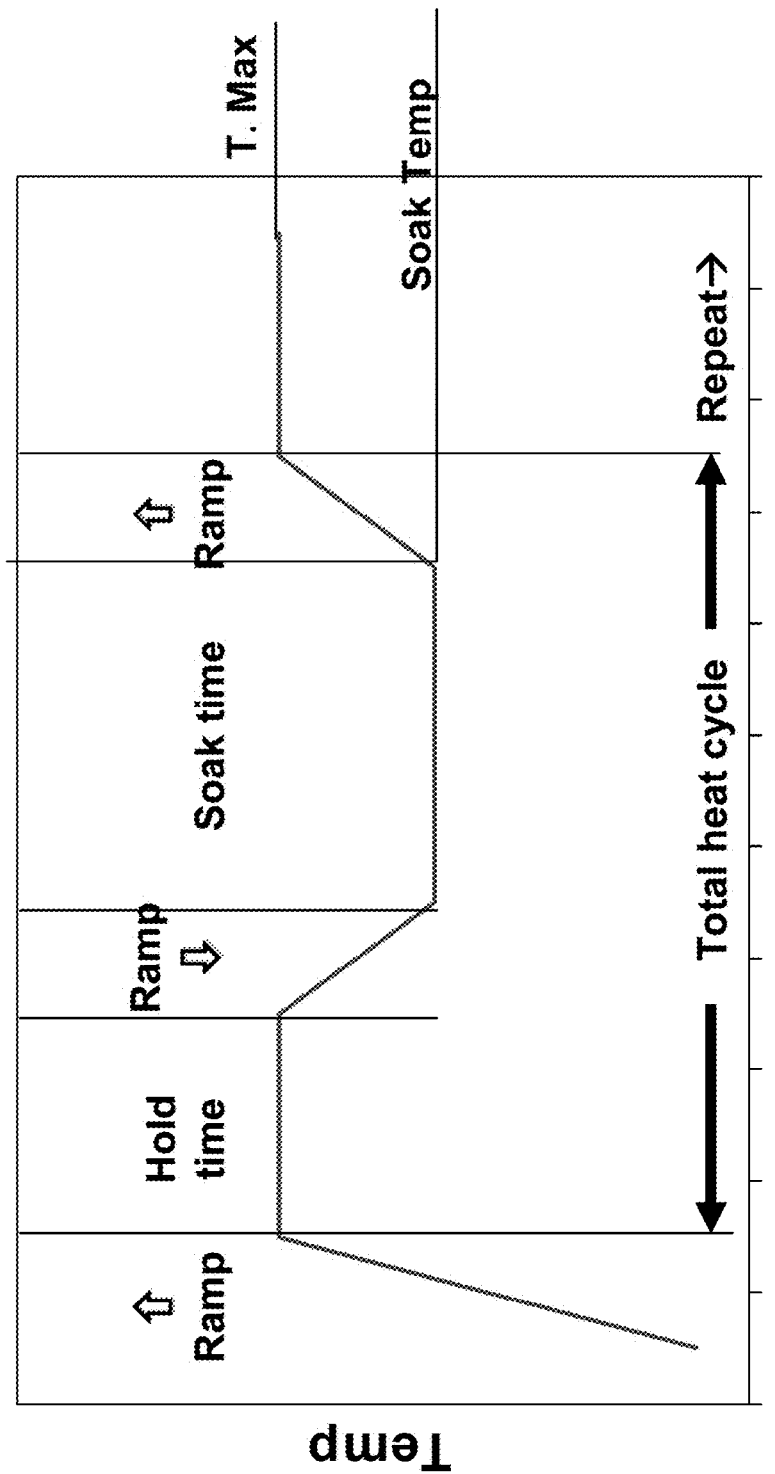
FIG. 13 is a graph of temperature versus time illustrating a variable heat cycle for the heating element, the variable heat cycle having a ramp-up phase, a peak-time hold phase, a release phase, and a soak phase in accordance with an embodiment of the invention.
Figure 14:
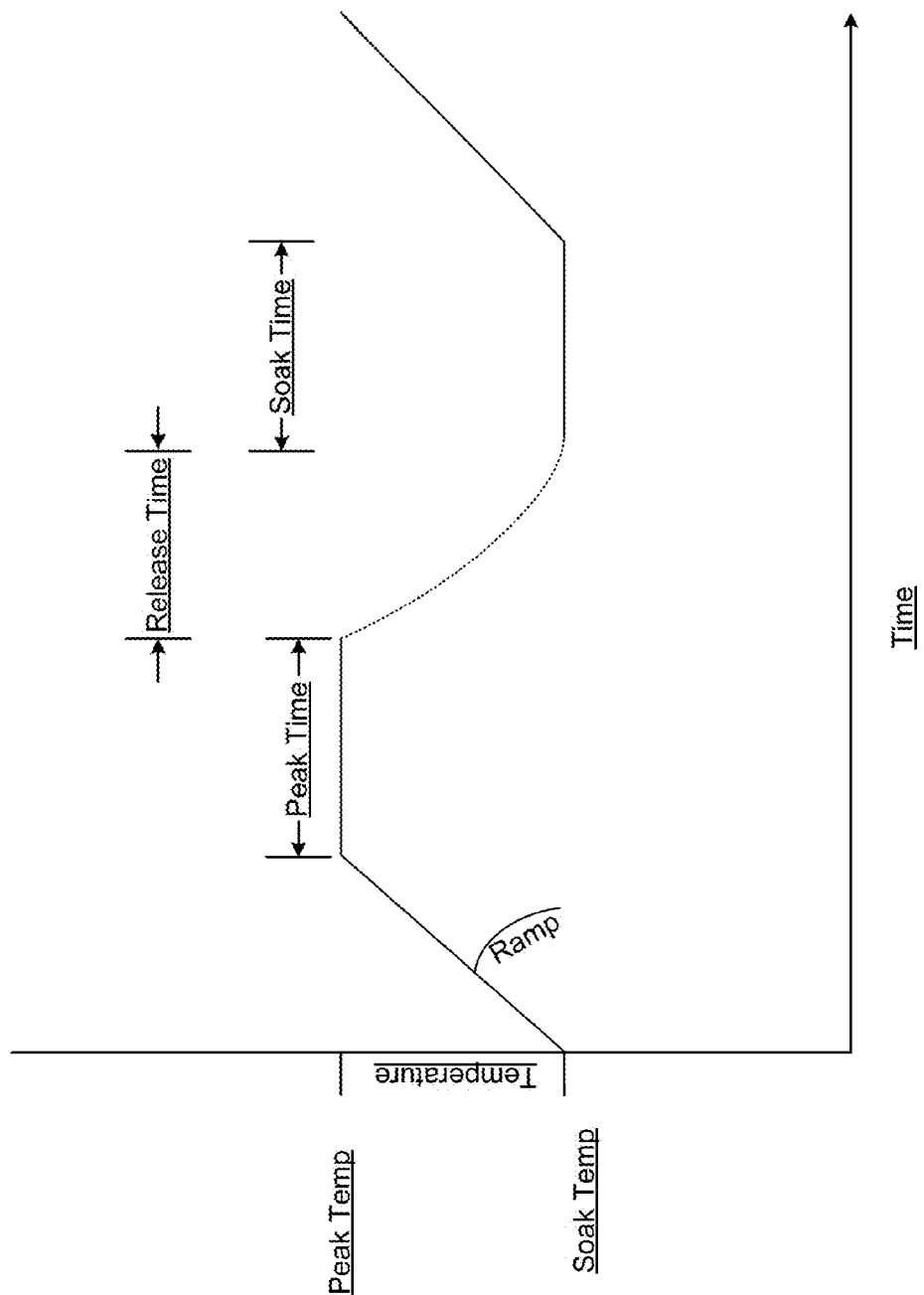
FIG. 14 is a graph of temperature versus time illustrating a variable heat cycle for the heating element, the variable heat cycle having a therapeutic temperature hold phase, a ramp-down phase, a soak phase, and a ramp-up phase in accordance with an embodiment of the invention.

FIG. 13 is a graph of temperature versus time illustrating a variable heat cycle for the heating element, the variable heat cycle having a therapeutic temperature hold phase, a ramp-down phase, a soak phase, and a ramp-up phase in accordance with an embodiment of the invention. FIG. 14 is a graph of temperature versus time illustrating a variable heat cycle for the heating element, the variable heat cycle having a ramp-up phase, a peak-time hold phase, a release phase, and a soak phase in accordance with an embodiment of the invention. The variable heat cycle shown in FIGS. 13 and 14 provides many advantages to the user. One advantage is an increased effectiveness of the thermal stimulation because the variable heat cycle prevents the nervous system receptors from accommodating to the thermal stimulation. For example, when a steady state heat is delivered, over time the thermal nerve receptors accommodate the thermal stimulation and emit a reduced response, thus reducing or eliminating the therapeutic effect of the thermal stimulation. When the variable heat cycle of the current embodiment is delivered, the thermal nerve receptors are not given time to accommodate to the thermal stimulation before the thermal stimulation is reduced, and therefore, the nerve receptors are reactivated with each variable heat cycle.

Without being bound by theory, the present invention provides thermal stimulation to the skin of a user; the thermal stimulation provides pain relief to the nervous system by stimulating the nervous system, but not allowing the thermal nerve receptors time to accommodate to the stimulation. In general, the nervous system is continuously attempting to accommodate to stimulants. When presented with a stimulant, the nervous system will react to the stimulant with a nerve response. Over time, the nervous system accommodates to the stimulation and provides a lesser response to the stimulation. However, if the stimulation is applied and then removed or reduced to allow the nervous system to reset or return to a baseline response mode, the thermal nerve receptors are not given the opportunity to accommodate to the stimulation and thus react anew to each introduction of the stimulation.

Another advantage of the variable heat cycle is that multiple therapeutic methodologies are applied in one cycle, namely, inhibiting nociception and increasing blood flow. The direct thermal stimulation in the peak time or therapeutic temperature hold provides direct stimulation of the nerves through heat and thus provides a counter-irritant to pain. Additionally, the soak phase is held at a temperature higher than the basal body temperature of the user, thus allowing continued therapeutic effects by improving the blood flow to the region and providing muscle relaxation while allowing the thermal nerve receptors to return to a baseline response mode.

Yet another advantage of the variable heat cycle is reduced power demand and consumption during the ramp-down or release phase when the thermal device does not draw power from the power supply, or draws reduced power from the power supply. Reduced power consumption results in a more efficient device with a longer life cycle and provides cost savings.

Figure 15:
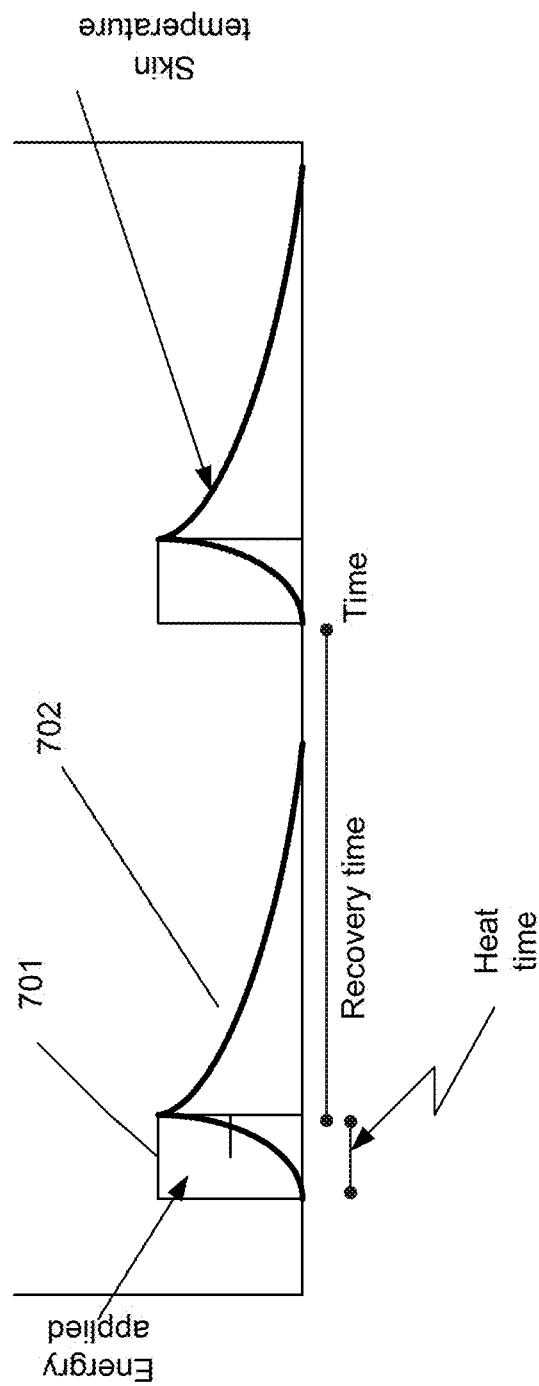
FIG. 15 is a graph of energy applied versus time illustrating the energy applied to the system and the resultant skin temperature wherein the bars represent energy delivered and the line indicates the skin temperature in accordance with an embodiment of the invention.

FIG. 15 is a graph of energy applied versus time illustrating the energy applied to the system and the resultant skin temperature wherein the bars represent energy delivered and the line indicates the skin temperature. In FIG. 15, bars 701 indicate on how long and how much energy is applied to the heat pads. The heat applied is measured on an arbitrary scale on the left lines 702 indicates estimated skin temperature for each profile and the skin temperature is indicated on an arbitrary scale on the right.

Figure 16:
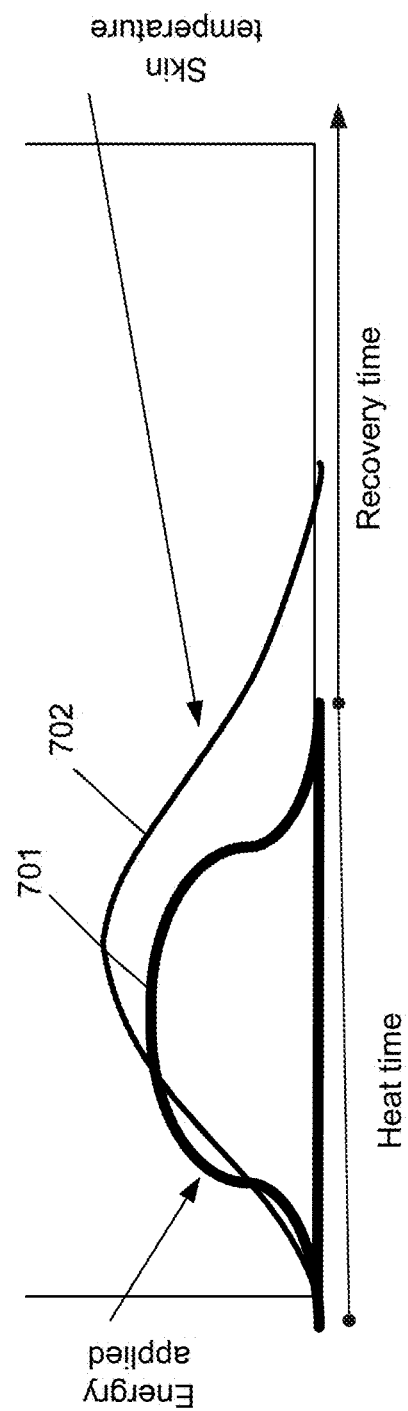
FIG. 16 is a graph of energy applied versus time illustrating a sine wave energy applied pattern and the resultant skin temperature in accordance with an embodiment of the invention.

FIG. 16 is a graph of energy applied versus time illustrating a sine wave energy applied pattern and the resultant skin temperature in accordance with an embodiment of the invention. This could be substituted with a square, crescendo, de-crescendo, intermittent or any other conceivable pattern. Thus, there are at least four variables that can be adjusted to ensure optimal analgesia; duration of heating "heat time, "recovery times" between heat times, intensity of heating, pattern of heating (sine wave (as shown in FIG. 16), square wave, saw tooth etc).

Figure 17:
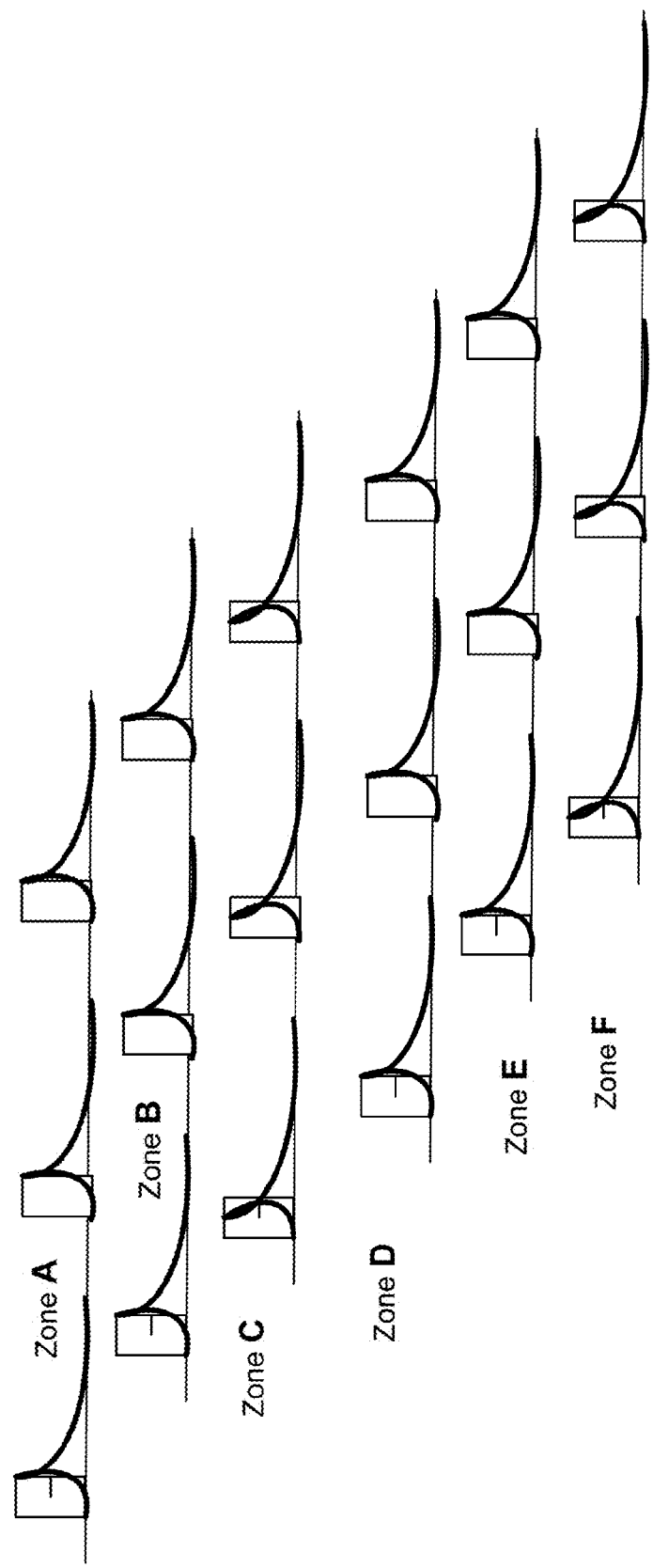
FIG. 17 illustrates energy applied to exemplary thermal zones A, B, C, D, E and the resultant skin temperature in an illustrative cascading pattern for a heating element with thermal zones or regions in accordance with an embodiment of the invention.

FIG. 17 illustrates energy applied to exemplary thermal zones A, B, C, D, E and the resultant skin temperature in an illustrative cascading pattern for a heating element with thermal zones or regions. The sequence is for demonstration only; the system can deliver any conceivable pattern.

In alternative embodiments, heat can be applied in a non-uniform manner. Taking advantage of individually controllable heat regions or heat zones the heat can be applied sequentially or in any other imaginable pattern. Sequential heating of individual heat regions as drawn in FIG. 7 would enable an entirely different therapeutic sensation to be achieved as compared with heating them all at the same time.

FIG. 17 shows an alternative embodiment where letters A, B, C, D, E represents physical zones of a heat element such as illustrated in FIG. 5. The diagram is intended to illustrate how heat is being applied to each zone in a sequential pattern. As energy is applied to zone A, while zone B, then zone B heats while A is resting and then zone C heats while zone D is and so forth. This has the effect of a wave of heat being passed from zone A to zone E and back again. The principle of moving heat zones can be applied vertically horizontally or both to achieve a checkerboard effect or any other conceivable pattern.

Figure 18:
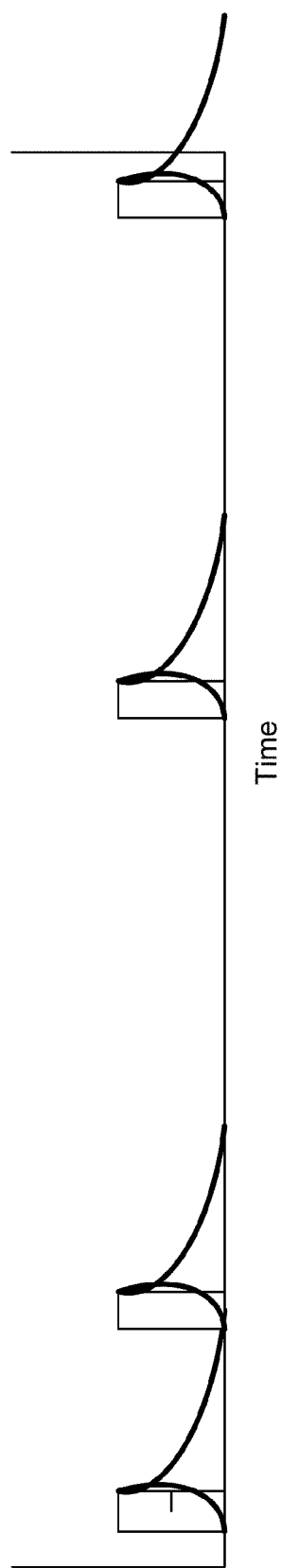
FIG. 18 illustrates an on-demand pattern of variable heat cycles over time as requested by a subject in accordance with an embodiment of the invention.

FIG. 18 illustrates an on demand pattern of variable heat cycles over time as requested by a subject. An alternative embodiment involves use of Patient Controlled Thermalgesia (PCT) illustrated by FIG. 18, where the patient can press an actuator such as a lever, a switch, a pressure sensor, or any other activation device as is known in the art, to demand heat on an as needed basis. FIG. 18 shows, on an arbitrary time base, the patient demanding analgesia four times. The pattern of heat delivered by the system could be constant or pre programmed onto the control unit.

One expected advantage of the system is that the heating device is portable and can be conveniently worn by the subject such that pain relief is available as needed. According to aspects of the invention, the device is designed to relieve pain or assist with healing in a variety of medical conditions such as low, mid, or upper back pain, muscular pain, dysmenorrhea, headaches, fibromyalgia, post-herpetic neuralgia, nerve injuries and neuropathies, injuries to extremities, and sprains and strains. Another expected advantage is that greater pain relief will be realized by the user because they will be able to control the frequency and duration of the treatment. Another expected advantage is increased efficacy of TENS when used in combination with the system described herein.

D. Study Results

A preclinical study done at the University of Washington with 15 subjects who suffered from chronic back pain demonstrated in randomized crossover design study that heat significantly improved the analgesic effectives of TENS. Heat alone was also significantly favored over TENS alone.

The current trial is a randomized controlled crossover design with a week washout between experimental sessions in subjects who suffer from chronic back pain. 11 of 50 subjects have completed all three experimental arms. The data to date shows that heat improves the analgesic effectiveness of TENS and Heat alone works better than TENS alone. The actual numbers are in the following table:

|  | Question 1 | Question 2 | Question 3 |
|---|---|---|---|
| Heat alone | 2.9 | 0.86 | 2.8 |
| TENS alone | 2.2 | 0.90 | 2.2 |
| Heat + TENS | 3.6 | 1.40 | 3.9 |

Question 1 result=the mean difference in pain ratings between pretreatment baseline and pain rating after 60 minutes of treatment. The pain scale ranges from 0-10. The larger the difference in pain ratings the better.

Question 2 result=the mean difference in pain ratings between pretreatment baseline and pain rating after 60 minutes of treatment. The pain rating scale is the descriptive pain scale. Again the larger the difference in pain ratings the better.

Question 3 result=the mean difference in pain ratings between pretreatment baseline and pain rating after 60 minutes of treatment. The pain assessment scale is the "pain unpleasantness rating scale". Again the larger the difference in pain ratings the better.

In summary:

The preclinical data clearly shows that heat improves the analgesia effectiveness of TENS in a randomized crossover study.

The current randomized controlled crossover study uses the actual heating device and assesses pain after 60 minutes of treatment using three different widely accepted and validated pain measurement tools. In all three assessments Heat+TENS is the most effective pain treatment and in 2 of 3 conditions heat alone works better than TENS alone in reducing pain.

E. Conclusion

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. The teachings of the invention provided herein can be applied to other systems, not necessarily the system described above. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

These and other changes can be made to the invention in light of the above Detailed Description. While the above description details certain embodiments of the invention and describes the best mode contemplated, no matter how detailed the above appears in text, the invention can be practiced in many ways. Details of the system may vary considerably in its implementation details, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

We claim:

1. A heating device for therapeutically heating skin to reduce accommodation of thermal nerve receptors, comprising:
    a heat delivery element adapted to be worn proximate to the skin of a user; and
    a microprocessor control unit configured to control the heat delivery element;
    wherein the microprocessor control unit is programmed to maintain at least one cycle of skin temperature having:
        a ramp-up temperature period,
        a peak temperature,
        a ramp-down temperature period, and
        a soak temperature,
        wherein the soak temperature is lower than the peak temperature, and wherein the soak temperature is greater than a body temperature.

2. The heating device of claim 1 wherein the peak temperature and the soak temperature are generally constant.

3. The heating device of claim 1 wherein the heat delivery element has independently-activated thermal zones, and wherein the thermal zones are activated in a predetermined pattern.

4. The heating device of claim 3 wherein the predetermined pattern is a checkerboard pattern, a sequential bar pattern, a wave pattern and/or a random pattern across the heat delivery element.

5. The heating device of claim 1 wherein the at least one cycle is initiated by the user.

6. The heating device of claim 1, further comprising a TENS system for providing a user relief from pain through electrical stimulation.

7. The heating device of claim 1, further comprising a thermal sensing element for sensing temperature of the heating element and/or of the skin.

8. The heating device of claim 1, further comprising an analgesic cream, creams and other topical medications used to treat nerve injuries, a nonsteroidal anti-inflammatory drug (NSAID) a cream used to treat nerve injuries, and/or an Opioid analgesic applied to the skin.

9. The heating device of claim 1 wherein the microprocessor control unit is wirelessly coupled to the portable heat delivery element.

10. The device of claim 1 wherein the heat delivery elements delivers a saw tooth wave energy pattern during at least one of the peak temperature and the soak temperature.

11. A user-controllable therapeutic heating device for relieving pain, comprising:
    a plurality of spaced apart thermal elements for heating skin, the thermal elements having a heat exchange surface in thermal communication with the skin;
    a power source electrically coupled to the plurality of spaced apart thermal elements; and
    a control unit operatively coupled to the thermal elements, the control unit allowing the user to activate the thermal elements for a temperature cycle and/or pattern, the temperature cycle and/or pattern having at least:
        a ramp-up temperature period,
        a peak temperature,
        a ramp-down temperature period, and
        a soak temperature, wherein the soak temperature is lower than the peak temperature, and wherein the soak temperature is above body temperature.

12. The user-controllable therapeutic heating device of claim 11 wherein the power source is contained in a housing that is releasably attachable to a user.

13. The user-controllable therapeutic heating device of claim 11 wherein the power source is wirelessly rechargeable.

14. The user-controllable therapeutic heating device of claim 11 wherein the temperature differential between the peak temperature and the soak temperature is less than 5° C.

15. The heating device of claim 11 wherein the peak temperature and the soak temperature are generally constant.

16. The user-controllable therapeutic heating device of claim 11 wherein the control unit further comprises a plurality of predetermined pattern durations, wherein multiple temperature cycles occur during one predetermined pattern duration.

17. The user-controllable therapeutic heating device of claim 11 wherein the heat exchange surface of the thermal element is affixed to the skin with a gel.

18. The user-controllable therapeutic heating device of claim 17 wherein the gel further includes an analgesic topical agent.

19. The user-controllable therapeutic heating device of claim 11 wherein the thermal elements are contained by an elastomeric band configured to fit a knee, an ankle, a foot, an elbow, a wrist, a joint, a shoulder, a neck and/or a head.

20. The user-controllable therapeutic heating device of claim 11 wherein the control unit is wirelessly coupled to the thermal elements.

21. The user-controllable therapeutic heating device of claim 11 wherein the control unit further includes at least one switch for activating the thermal elements.

22. The user-controllable therapeutic heating device of claim 11 wherein the thermal elements are independently activated.

23. The device of claim 11 wherein the spaced apart thermal elements execute the temperature cycle and/or pattern that is generally same for all the thermal elements.

24. The device of claim 11 wherein the spaced apart thermal elements execute the temperature cycles and/or patterns that are shifted in time.

25. The heating device of claim 11, further comprising a temperature sensing element proximate to the heat exchange surface.

26. The heating device of claim 11, further comprising:
a first temperature sensing element proximate to the heat exchanging surface for detecting a first temperature of the heat exchange surface; and
a second temperature sensing element proximate to the heat exchanging surface for detecting a second temperature of the skin of the user.

27. A method of using heat to reduce accommodation of thermal nerve receptors on skin of a user, comprising:
(i) providing at least one heating element that is removably attachable proximate to the skin of the user;
(ii) increasing a temperature of the heating element to provide a first temperature ramp-up period;
(iii) holding the temperature of the heating element at a first therapeutic level;
(iv) decreasing the temperature of the heating device during a ramp-down period; and
(v) holding the temperature of the heating device at a second predetermined soak level, wherein the soak level temperature is lower than the first therapeutic level temperature, and wherein the soak level temperature is above a normal body temperature.

28. The method of claim 27, further comprising:
reducing accommodation of thermal nerve receptors of a first region on the skin of the user by performing (i)-(v) at the first region; and
reducing accommodation of thermal nerve receptors of a second region on the skin of the user by performing (i)-(v) at the second region.

29. The method of claim 27, further comprising:
repeating (ii)-(v) for a predetermined duration of time.

30. The method of claim 27, further comprising measuring skin temperature and/or heating device temperature with a thermal sensing element.

31. The method of claim 27, further comprising:
providing a TENS therapy system comprising a TENS generator for supplying TENS pulses to the user and a synchronizing circuit to synchronize the application of TENS pulses and electroporation pulses to the user.

* * * * *